US00PP09223P

United States Patent [19]

Meilland

[11] Patent Number: Plant 9,223

[45] Date of Patent: Aug. 1, 1995

[54] HYBRID TEA ROSE PLANT NAMED 'MEIGAFOR'

[75] Inventor: Alain A. Meilland, Antibes, France

[73] Assignee: The Conard-Pyle Company, West Grove, Pa.

[21] Appl. No.: 314,388

[22] Filed: Sep. 28, 1994

[51] Int. Cl.[6] ..... A01H 5/00

[52] U.S. Cl. ..... Plt./15

[58] Field of Search ..... Plt. 11, 14, 15

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and continuously forms attractive double light Creamy White blossoms. Such blossoms are long-lasting and initially exhibit an urn-shaped configuration. The plant exhibits an erect growth habit, strong vegetation, decorative glossy foliage, and is well suited for use in the production of cut flowers. Additionally, the plant exhibits excellent disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the cross of the OMEGA variety (non-patented in the United States) and the JELPIROFOR variety (U.S. Plant Pat. No. 5,632). The male parent (i.e., the pollen parent) was the MEIVAMO variety (U.S. Plant Pat. No. 8,619). The Parentage of the new variety can be summarized as follows:

(OMEGA×JELPIROFOR)×MEIVAMO.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance double light Creamy White blossoms that initially assume an urn-shaped configuration and are lightly suffused with light Chartreuse Green,
(b) is particularly suited for cut flower production, and
(c) exhibits excellent disease resistance.

The new variety well meets the needs of the horticultural industry and is particularly well suited for use when producing cut flowers under green house conditions.

The new variety has been found to undergo asexual propagation in France by a number of routes, including budding, grafting, and cuttage. The characteristics of the new variety have been found by such methods in France to be stable and to be strictly transmissible from one generation to another.

The new variety has been named the MEIGAFOR variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during May while budded on *Rosa indica* understock and growing in greenhouses at Cap d' Antibes, France.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG.. 6—illustrates a specimen of an open flower — plan view—obverse;

FIG. 7—illustrates a specimen of a fully open flower—plan view—obverse;

FIG. 8—illustrates a specimen of a floral receptacle showing the arrangement of the stamens and pistils;

FIG. 9—illustrates a specimen of a floral receptacle showing the arrangement of the pistils (stamens removed);

FIG. 10—illustrates a specimen of a flowering stem;

FIG. 11—illustrates a specimen of a main branch;

FIG. 12—illustrates a specimen of a leaf with three leaflets—plan view—upper surface;

FIG. 13—illustrates a specimen of a leaf with five leaflets—plan view—under surface; and FIG. 14—illustrates a specimen of a leaf with seven leaflets—plan view — upper surface.

DETAILED DESCRIPTION

Figures 1, 2, 3, 4, 5, 6, 7, 8, 9, 10, 11, 12, 13, 14:
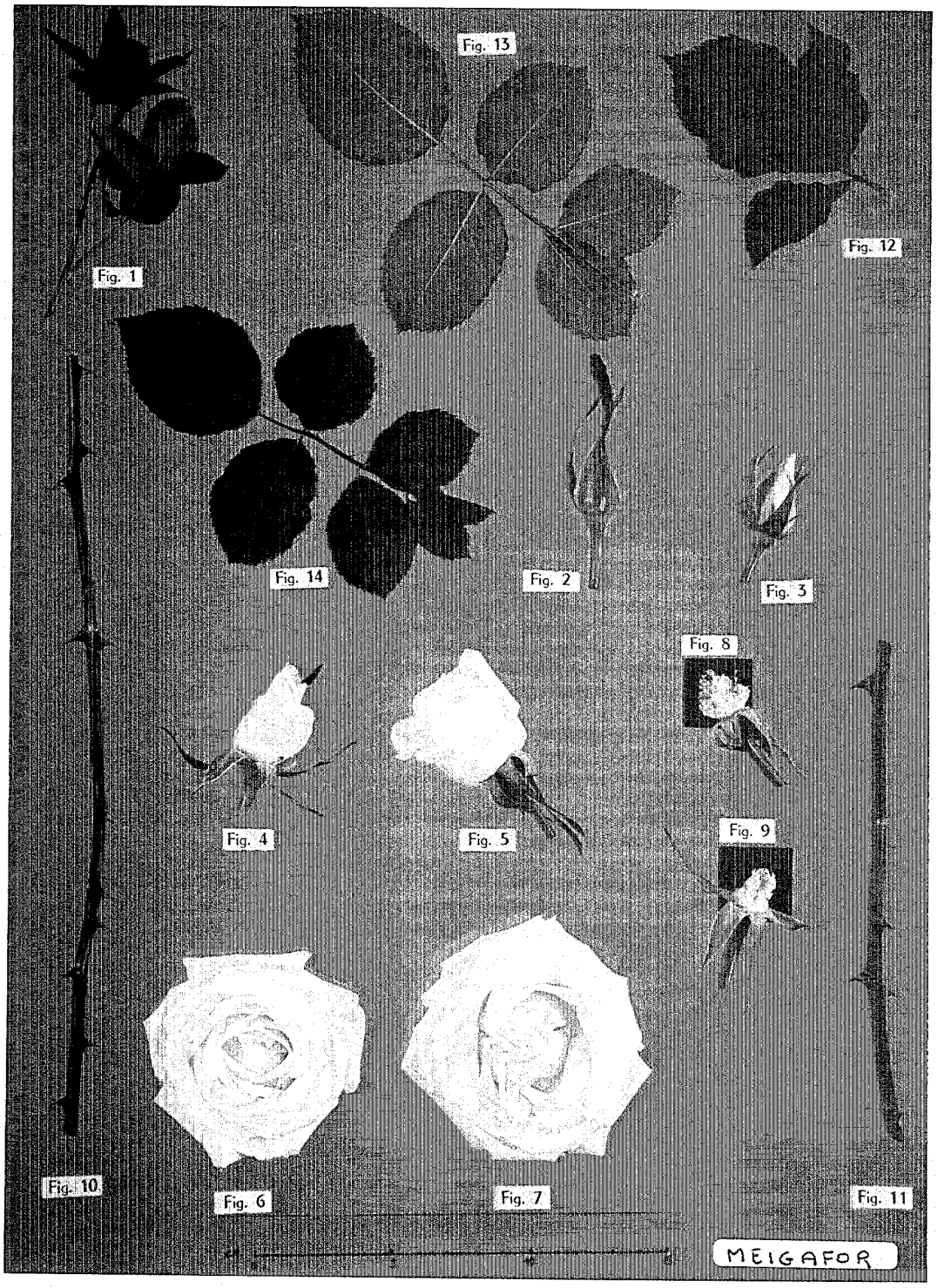

The chart used in the identification of the colors is that of The Royal Horticultural Society (R.H.S. Colour Chart). The description is based on the observation of two year-old plants while budded on *Rosa indica* understock and growing during May in greenhouses at Cap d' Antibes, France. The coloration in common terms precedes reference to the chart.

Class: Hybrid Tea.

Plant:

*Height.*—Approximately 50 to 80 cm. on average at the end of the growing season.

*Habit.*—Erect.

Branches:

*Color.*—Young stems: light green, Green Group 137B. Adult wood: light green, Green Group 143C.

*Thorns.*—Size: medium to small. Quantity: few. Color: reddish on young stems and greenish pinkish on mature wood.

Leaves:

*Stipules.*—Adnate, pectinate, very wide and linear.

*Petioles.*—Upper surface: striped reddish brown on young foliage, medium green on adult foliage, and very glandular. Under surface: light green and bear numerous small prickles.

*Leaflets.*—Number: 3, 5 (most often), and 7. Shape: rounded. Serration: simple and regular. Texture: consistent. General appearance: dense and glossy foliage. Color (young foliage): upper surface: reddish-brown. under surface: reddish-brown. Color (adult foliage): upper surface: dark green, Green Group 137A under surface: medium green, Green Group 138B.

Inflorescence:

*Number of flowers.*—Usually one flower per stem.

*Peduncle.*—Light green and more or less pubescent. The length is approximately 11 to 12 cm. on average.

*Sepals.*—Upper surface: tomentose, and greenish in coloration. Under surface: medium green, and more or less glandular and appendiculate at the edges.

*Buds.*—Shape: elongated. Length: approximately 4 cm. on average. Size: medium. Color upon opening: upper surface: Creamy White, Yellow Group 11D, and sometimes edged with light Neyron Rose, Red group 55C when cold growing conditions are encountered. under surface: Creamy White, Yellow-White Group 158D, and lightly suffused with light Chartreuse Green, Green-Yellow Group 1D, particularly at the base.

*Flower.*—Shape: initially urn-shaped, and subsequently cup-shaped. Diameter: approximately 12 to 13 cm. on average. Color (when opening begins): upper surface: Creamy White, Yellow Group 11D, and sometimes edges with Light Neyron Rose, Red Group 55C when cold growing conditions are encountered. under surface: Creamy White, Yellow Group 158D, and lightly suffused with light Chartreuse Green, Yellow-Green Group 1D. Color (when blooming): upper surface: Creamy White, Yellow Group 11D, and sometimes edges with light Neyron Rose, Red Group 55C when cold growing conditions are encountered. under surface: Creamy White, Yellow Group 11D, and sometimes edged with light Neyron Rose, Red Group 55C when cold growing conditions are encountered. Color (at end of opening): upper surface: Creamy White, Yellow Group 11D, and sometimes edged with light Neyron Rose, Red Group 55C when cold growing conditions are encountered. under surface: Creamy White, Yellow Group 11D, and sometimes edged with light Neyron Rose, Red Group 55C when cold growing conditions are encountered. Fragrance: slight. Lasting quality: very long when cut and placed in a vase. Petal number: approximately 35 on average. Petal shape: outer petals tend to be rounded and the inner petals tend to be oval. Petal drop: good. Stamen number: approximately 120 to 130 on average. Anthers: normal, ochre in coloration and tend to be disposed above the stigmas. Filaments: yellowish in coloration, and commonly of irregular heights. Pistils: approximately 96 to 108 on average. Stigmas: light ochre in coloration. Styles: fuchsine in coloration, and commonly of irregular heights. Receptacle: medium green, smooth, and in longitudinal section in the shape of a funnel.

Development:

*Vegetation.*—Strong.

*Blooming.*—Abundant.

Aptitude to bear fruits.—Excellent.

*Resistance to diseases.*—Excellent.

I claim:

1. A new and distinct variety of Hybrid Tea rose plant characterized by the following combination of characteristics:

(a) forms in abundance double light Creamy White blossoms that initially assume an urn-shaped configuration and are light suffused with light Chartreuse Green, (b) is particularly suited for cut flower production, and (c) exhibits excellent disease resistance;

substantially as herein shown and described.

* * * * *

MEIGAFOR